(12) United States Patent
Xing

(10) Patent No.: US 7,668,360 B2
(45) Date of Patent: Feb. 23, 2010

(54) IMAGE PROCESSING METHOD AND X-RAY CT SYSTEM

(75) Inventor: Zhanfeng Xing, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 700 days.

(21) Appl. No.: 11/531,899

(22) Filed: Sep. 14, 2006

(65) Prior Publication Data
US 2007/0058883 A1 Mar. 15, 2007

(30) Foreign Application Priority Data
Sep. 15, 2005 (CN) .......................... 2005 1 0109922

(51) Int. Cl.
*G06K 9/00* (2006.01)
*H04N 11/02* (2006.01)
(52) U.S. Cl. .................................. 382/131; 375/240.19
(58) Field of Classification Search ................. 382/128, 382/129, 130, 131, 132, 133, 134, 265, 275; 378/4, 21, 23, 24, 25, 26, 27, 28, 46, 90, 378/92, 98.4, 98.6, 98.9, 101, 140, 901; 375/240.19
See application file for complete search history.

(56) References Cited

U.S. PATENT DOCUMENTS 5,657,085 A 8/1997 Katto
6,141,452 A * 10/2000 Murao ......................... 382/240
6,233,357 B1 * 5/2001 Li et al. ....................... 382/248
6,361,501 B1 3/2002 Amano et al.
6,567,081 B1 5/2003 Li et al.
6,643,406 B1 * 11/2003 Hajjahmad et al. .......... 382/240
6,658,158 B2 * 12/2003 Fukuhara et al. ............ 382/240

FOREIGN PATENT DOCUMENTS

JP 2002-133399 5/2002

OTHER PUBLICATIONS

Stephane Mallat and Sifen Zhong; Characterization of Signals from Multiscale Edges; IEEE Transactions on Pattern Analysis and Machine Intelligence, vol. 14, No. 7, Jul. 1992; 710-732.

* cited by examiner

*Primary Examiner*—Abolfazl Tabatabai
(74) *Attorney, Agent, or Firm*—Armstrong Teasdale LLP

(57) ABSTRACT

An object of the present invention is to provide an image processing method for reducing noises without causing a side effect and an X-ray CT system that performs the image processing. An input image is wavelet-transformed using a gradient form. Resultant wavelet vectors are classified into categories of strongly edged objects, weakly edged objects, radial lines, and noises. The wavelet vectors classified into the category of strongly edged object are left intact. The wavelet vectors classified into the category of weakly edged objects have the directions thereof filtered. The wavelet vectors classified into the categories of radial lines and noises are smoothed. The resultant wavelet vectors are inverse-wavelet-transformed in order to produce an output image.

10 Claims, 9 Drawing Sheets

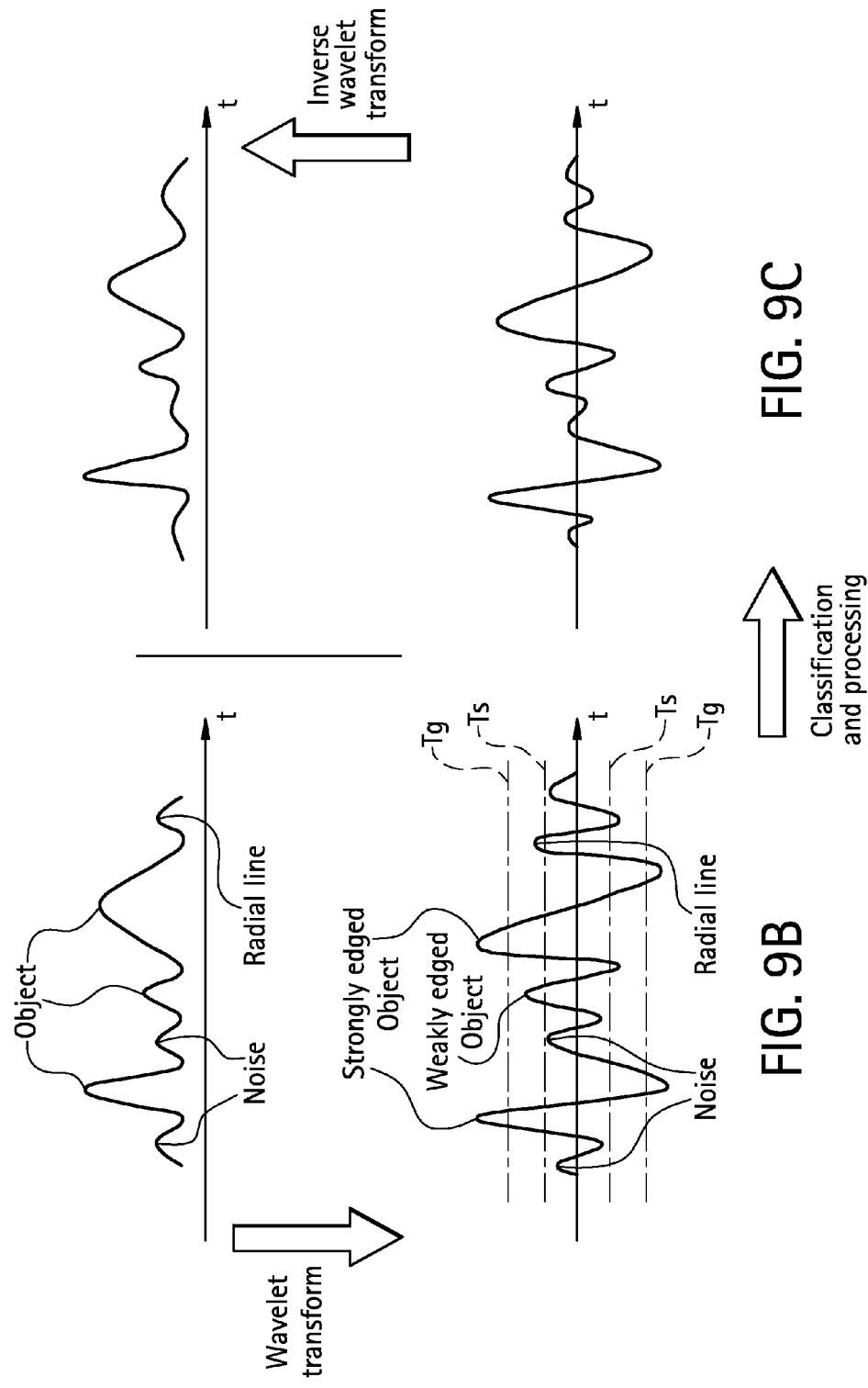

| Original image(sd) | Processed image(sd) |
|---|---|
| 2.2 | 1.6 |
| 2.1 | 1.5 |
| 2.7 | 2.0 |
| 2.2 | 1.6 |
| 1.9 | 1.3 |
| 2.22 (mean) | 1.60 (mean) |
| 28% reduction ||

Original Image    Processed Image

| Original image(LCD) | Processed image(LCD) |
|---|---|
| 0.0923 | 0.0933 |
| 0.0381 | 0.0385 |
| 0.0521 | 0.0530 |
| 1.4% increase ||

Original Image    Processed Image

| Original image(LP) | Processed image(LP) |
|---|---|
| 12 | 12 |
| Identical ||

Original Image    Processed Image

FIG. 13A
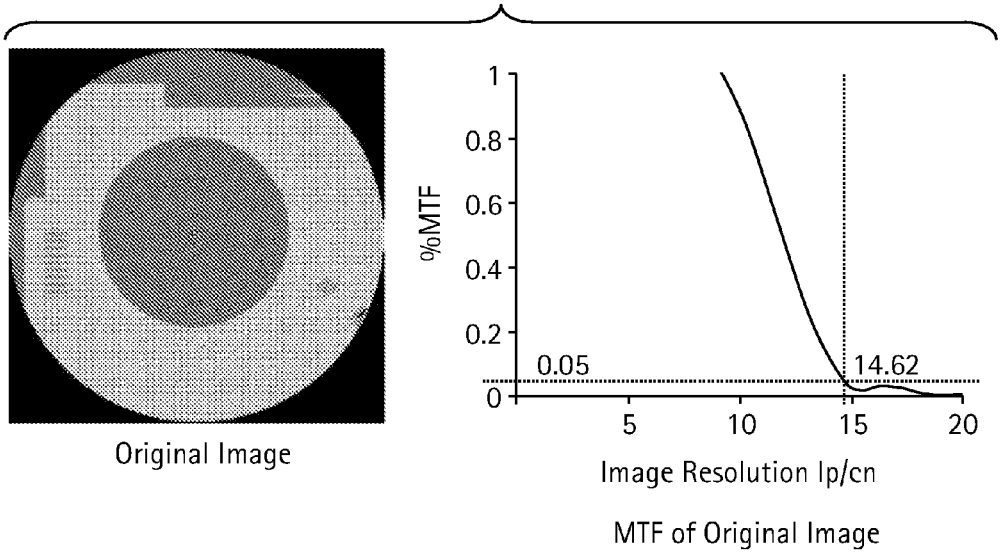
Original Image
MTF of Original Image
FIG. 13B
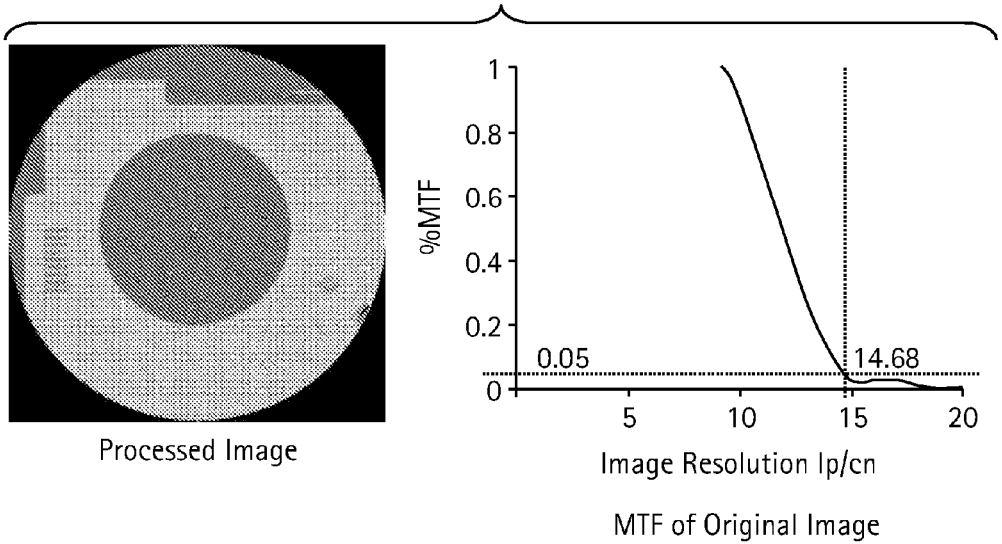
Processed Image
MTF of Original Image
FIG. 13C
| %MTF | Original image(LP) | Processed image(LP) |
|---|---|---|
| 50 | 11.86 | 11.86 |
| 20 | 13.40 | 13.40 |
| 10 | 14.06 | 14.06 |
| 5 | 14.62 | 14.68 |
| Identical | | |

US 7,668,360 B2

IMAGE PROCESSING METHOD AND X-RAY CT SYSTEM

CROSS REFERENCE TO RELATED APPLICATIONS

This application claims the benefit of Chinese Application No. 200510109922.7 filed Sep. 15, 2005.

BACKGROUND OF THE INVENTION

The present invention relates to an image processing method and an X-ray computed tomography (CT) system. More particularly, the present invention is concerned with a method of wavelet-transforming an image, reducing noises in the wavelet domain, and then inverse-wavelet-transforming the wavelet-domain image so as to restore the image, and an X-ray CT system that performs the image processing.

In X-ray CT systems, X-irradiation/detection equipment that rotates in a gantry acquires transmitted X-ray signals, which represent a plurality of views, from a subject, and tomographic images are reconstructed based on the transmitted X-ray signals. The rotation of the X-irradiation/detection equipment may be referred to as a scan. The acquired transmitted X-ray signal may be referred to as scan data.

A reconstructed image has noises therein reduced. One of noise reduction methods is such that an image is wavelet-transformed, the resultant wavelet-domain signal has noises thereof reduced, and the resultant signal is then inverse-wavelet-transformed in order to restore the image. The noise reduction in the wavelet domain is achieved by replacing signal components, of which levels fall below a predetermined threshold, with 0s (refer to, for example, Japanese Unexamined Patent Publication No. 2002-133399 (p.3, FIG. 1 to FIG. 7).

The foregoing noise reduction method of simply replacing signal components, of which levels fall below a predetermined threshold, with 0s causes a restored image to suffer a shift in a CT number, deformation of edges, an abrupt change, or any other side effect.

An object of the present invention is to provide an image processing method for reducing noises without causing a side effect and to provide an X-ray CT system that performs the image processing.

SUMMARY OF THE INVENTION

According to one aspect of the present invention for accomplishing the foregoing object, there is provided an image processing method in which: an input image is wavelet-transformed using a gradient form; resultant wavelet vectors are classified into categories of strongly edged objects, weakly edged objects, radial lines, and noises; wavelet vectors classified into the category of strongly edged objects are left intact; wavelet vectors classified into the category of weakly edged objects have the directions thereof filtered; and wavelet vectors classified into the categories of radial lines and noises are smoothed; the resultant wavelet vectors are inverse-wavelet-transformed in order to produce an output image.

According to another aspect of the present invention for accomplishing the foregoing object, there is provided an X-ray CT system comprising a data acquisition means for acquiring data by scanning a subject with X-rays, an image reconstruction means for reconstructing an image according to the acquired data, and an image processing means for processing the reconstructed image. The image processing means comprises: a transforming means for wavelet-transforming an input image using a gradient form; a classifying means for classifying resultant wavelet vectors into categories of strongly edged objects, weakly edged objects, radial lines, and noise; a processing means for leaving wavelet vectors, which are classified into the category of strongly edged objects, intact, filtering the directions of wavelet vectors classified into the category of weakly edged objects, and smoothing wavelet vectors that are classified into the categories of radial lines and noise; and an image production means for inverse-wavelet-transforming the resultant wavelet vectors so as to produce an output image.

Preferably, the classification employs a first threshold concerning the magnitude of a vector, a second threshold smaller than the first threshold, and a third threshold concerning the regulation in the direction of a vector. Wavelet vectors whose magnitudes are larger than the first threshold are classified into the category of strongly edged objects. Wavelet vectors whose magnitudes are equal to or smaller than the first threshold and larger than the second threshold and whose regulations in directions thereof are larger than the third threshold are classified into the category of weakly edged objects. Wavelet vectors whose magnitudes are equal to or smaller than the first threshold and whose regulations in directions thereof are equal to or smaller than the third threshold are classified into the category of radial lines. Wavelet vectors whose magnitudes are equal to or smaller than the second threshold are classified into the category of noises. Thus, the classification can be achieved appropriately.

Preferably, the regulation in the direction of a vector is expressed as a ratio of a mean vector, which is a mean of a center vector located in the center of a window defined with a matrix of 3 by 3 and two ambient vectors whose directions from the center vector is the smallest, to a means vector that is a mean of all vectors within the window. Thus, the regulation is expressed simply.

Preferably, the filtering of directions is achieved by sampling a combination of a center vector, which is located in the center of a window defined with a matrix of 3 by 3, and two ambient vectors the sum of whose differences from the center vector is the smallest, and replacing the center vector with a mean vector that is a mean of the two ambient vectors and the center vector.

Preferably, the smoothing of vectors is achieved by replacing a center vector, which is located in the center of a window defined with a matrix of 3 by 3, with a mean vector that is a mean of all vectors in the window.

According to the foregoing aspects of the present invention, an input image is wavelet-transformed using a gradient form. Resultant wavelet vectors are classified into categories of strongly edged objects, weakly edged objects, radial lines, and noises. The wavelet vectors classified into the category of strongly edged objects are left intact. The wavelet vectors classified into the category of weakly edged objects have the directions thereof filtered. The wavelet vectors classified into the categories of radial lines and noises are smoothed. The resultant wavelet vectors are inverse-wavelet-transformed in order to produce an output image. Consequently, there are provided an image processing method for reducing noises without causing a side effect and an X-ray CT system that performs the image processing.

BRIEF DESCRIPTION OF THE DRAWINGS

FIGS. 9a, 9b, 9c, and 9d show the concept of image processing that is an example of the best mode for implementing the present invention.

FIGS. 13a-13c show comparison between an original image and a processed image using partly half-tone photographs.

DETAILED DESCRIPTION OF THE INVENTION

Figure 1:
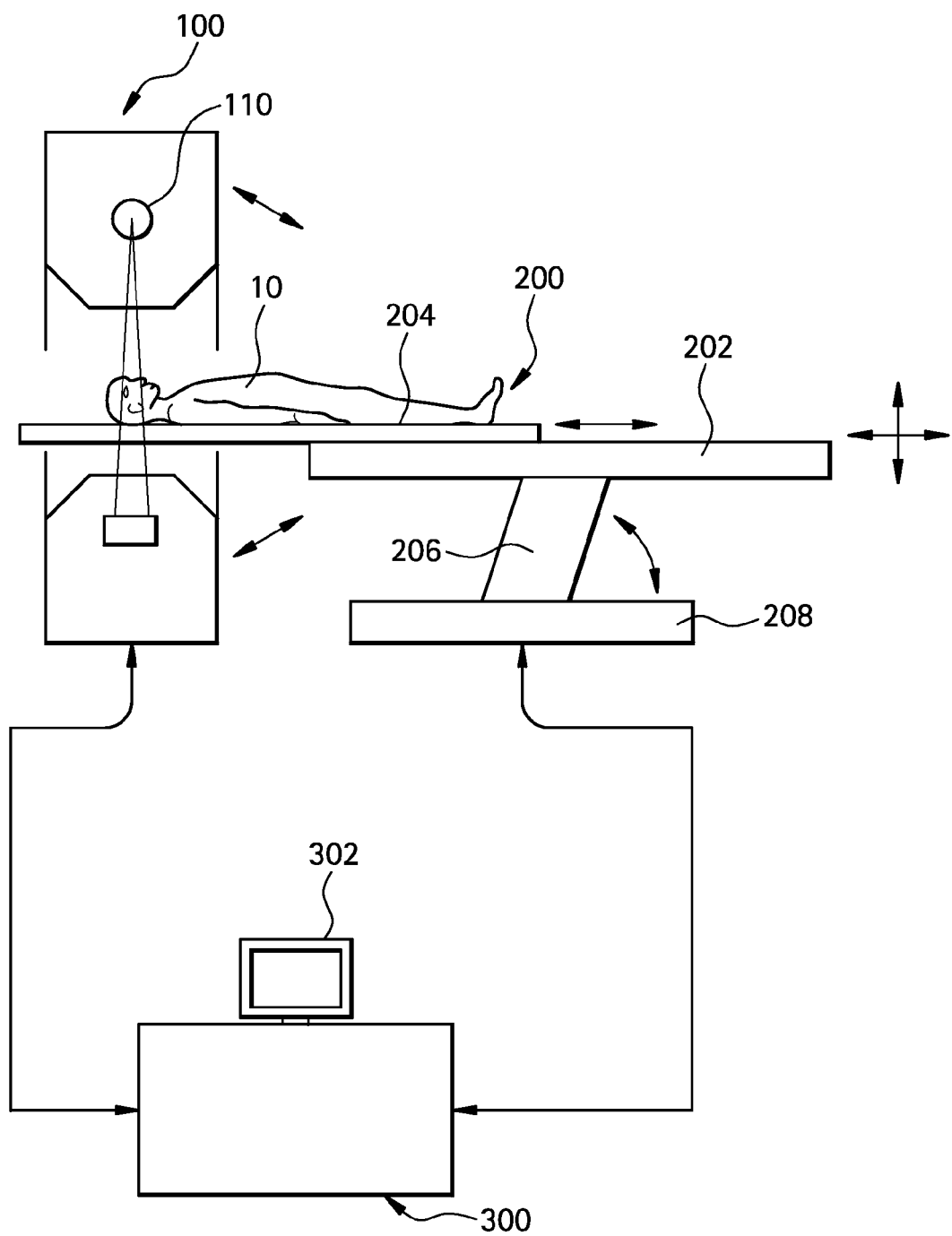
FIG. 1 shows the configuration of an X-ray CT system that is an example of the best mode for implementing the present invention.

The best mode for implementing the present invention will be described with reference to drawings below. The present invention will not be limited to the best mode for implementing the present invention. FIG. 1 illustratively shows the configuration of an X-ray CT system. The X-ray CT system is an example of the best mode for implementing the present invention. The configuration of the X-ray CT system presents an example of the best mode for implementing the present invention in an X-ray CT system. Moreover, actions to be performed in the X-ray CT system present an example of the best mode for implementing the present invention in an image processing method.

An X-ray CT system comprises a gantry 100, a table 200, and an operator console 300. The gantry 100 uses X-irradiation/detection equipment 110 to scan a subject 10 who is carried while lying down on the table 200, acquires transmitted X-ray signals (scan data items) representing a plurality of views, and transfers the views to the operator console 300. The gantry 100 is an example of a data acquisition means included in the present invention.

The operator console 300 reconstructs an image according to the scan data received from the gantry 100, reduces noises contained in the reconstructed image, and displays a processed image on a display 302. The operator console 300 is an example of an image reconstruction means included in the present invention. Moreover, the operator console 300 is an example of an image processing means included in the present invention.

The operator console 300 controls the movements of the gantry 100 and the table 200 alike. Under the control of the operator console 300, the gantry 100 scans a subject under predetermined scan conditions, and the table 200 positions the subject 10 so that a predetermined region will be scanned. The positioning is such that an incorporated alignment mechanism adjusts the height of a tabletop 202 and the distance of a horizontal movement made by a cradle 204 placed on the tabletop.

When a subject is scanned with the cradle 204 at a halt, axial scan is achieved. By continuously scanning a subject a plurality of times while continuously moving the cradle 204, helical scan is achieved. Every time the cradle 204 is brought to a halt while intermittently moved, if a subject is scanned, cluster scan is achieved.

For adjustment of the height of the tabletop 202, a support column 206 is swung with the root of the support column fixed to a base 208 as a center. Along with the swing of the support column 206, the tabletop 202 is displaced in vertical and horizontal directions. The cradle 204 is moved horizontally on the tabletop 202, whereby the horizontal displacement of the tabletop 202 is canceled out. Depending on the scan conditions, a subject is scanned with the gantry 100 tilted. The gantry 100 is tilted by an incorporated tilt mechanism.

Figure 2:
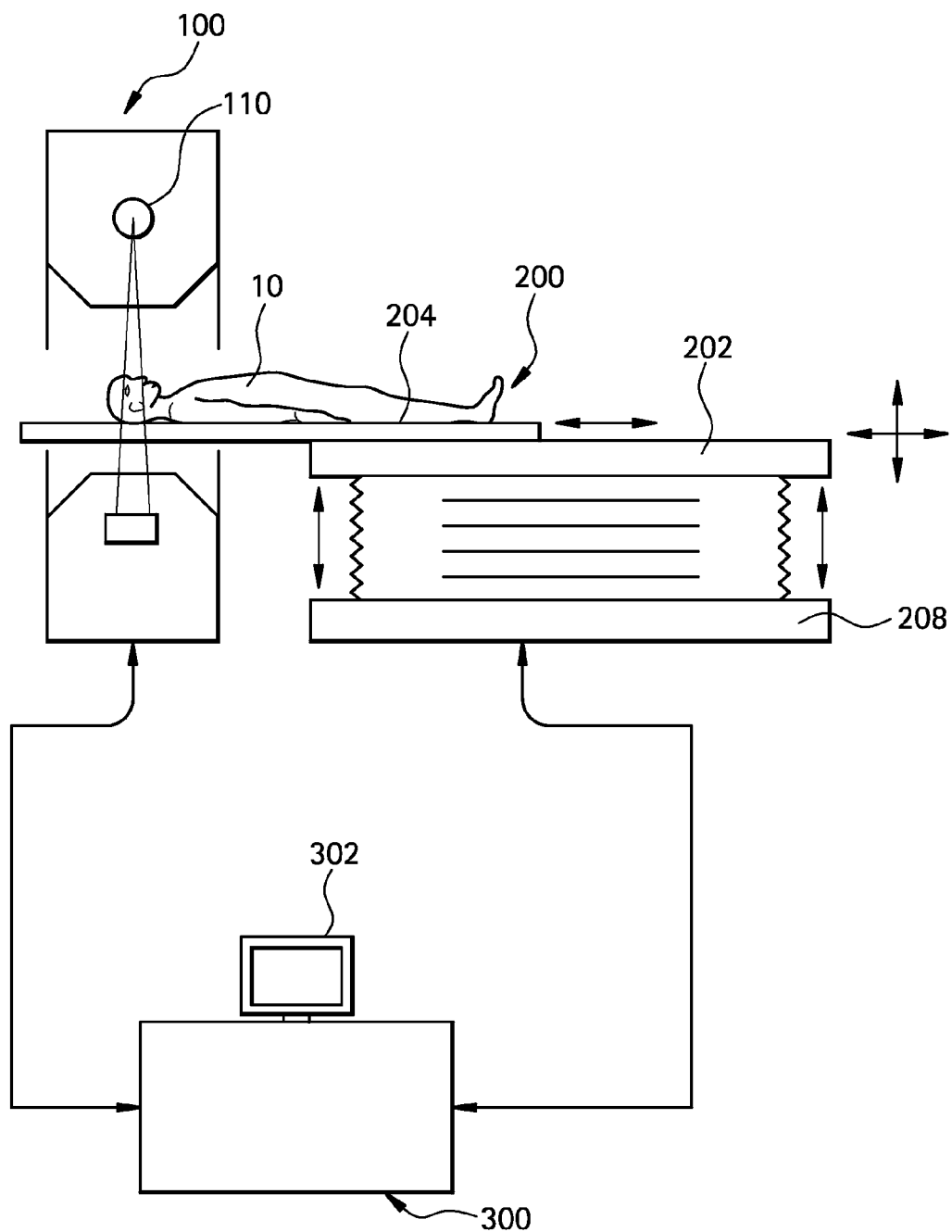
FIG. 2 shows the configuration of an X-ray CT system that is an example of the best mode for implementing the present invention.

Incidentally, the table 200 may be, as shown in FIG. 2, of a type having the tabletop 202 thereof lifted or lowered vertically with respect to the base 208. The tabletop 202 is lifted or lowered by an incorporated lifting/lowering mechanism. The tabletop 202 of the table 200 will not be horizontally moved along with the lifting or lowering.

Figure 3:
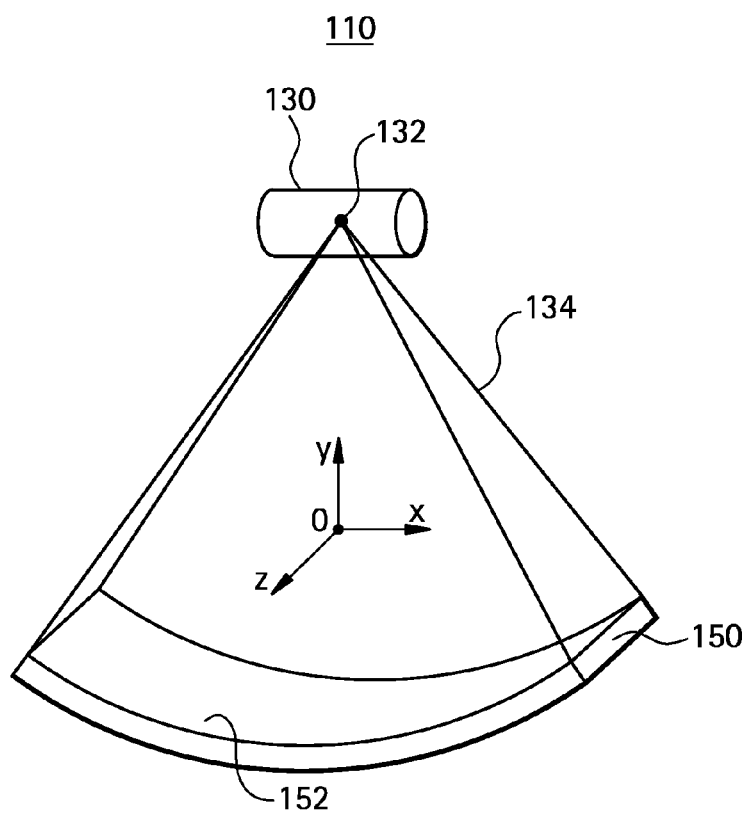
FIG. 3 shows the configuration of X-irradiation/detection equipment.

FIG. 3 illustratively shows the configuration of the X-irradiation/detection equipment 110. The X-irradiation/detection equipment 110 uses an X-ray detector 150 to detect X-rays 134 radiated from a focal spot 132 in an X-ray tube 130.

The X-rays 134 are recomposed by a collimator that is not shown into cone-beam or fan-beam X-rays that are laterally symmetrical. The X-ray detector 150 has an X-ray incidence surface 152 that spreads two-dimensionally in line with the spread of X-rays. The X-ray incidence surface 152 is curved like part of a cylinder whose center axis passes through the focal spot 132.

The X-irradiation/detection equipment 110 rotates about a center axis passing through an isocenter that is a center of radiography. The center axis is parallel to the center axis of the cylinder part of which is formed by the X-ray detector 150.

The direction of the center axis of the rotation shall be regarded as a z direction, the direction of a line linking the isocenter O and the focal spot 132 shall be regarded as a y direction, and the direction perpendicular to the z and y directions shall be regarded as an x direction. The axes extending in the x, y, and z directions respectively serve as three axes of a rotating coordinate system having the z axis as a center axis.

Figure 4:
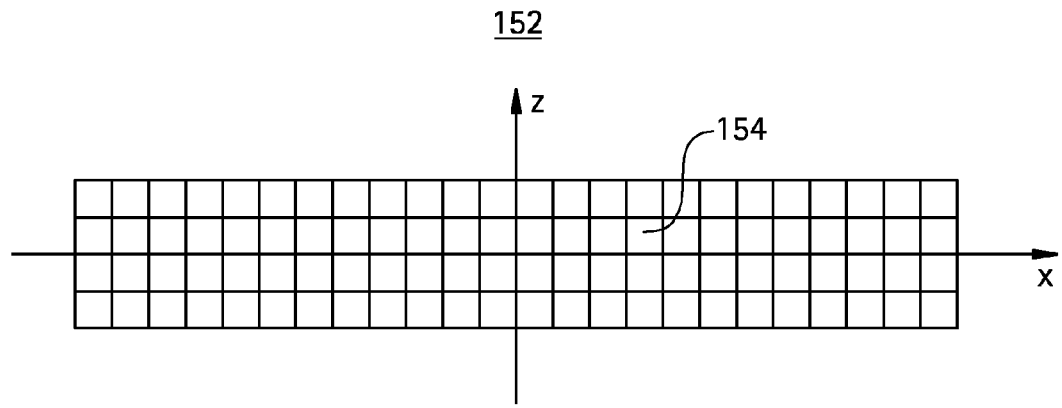
FIG. 4 shows the structure of an X-ray incidence surface of an X-ray detector.

FIG. 4 is a plan view illustratively showing the X-ray incidence surface 152 of the X-ray detector 150. The X-ray incidence surface 152 has detection cells 154 two-dimensionally arranged in the x and z directions. In other words, the X-ray incidence surface 152 is realized with a two-dimensional array of detection cells 154. When fan-beam X-rays are employed, the X-ray incidence surface 152 may be realized with a one-dimensional array of detection cells 154.

The individual detection cells 154 provide the X-ray detector 150 with detection channels. The X-ray detector 150 is therefore a multi-channel X-ray detector. The detection cells 154 are each composed of, for example, a scintillator and a photodiode.

Figure 5:
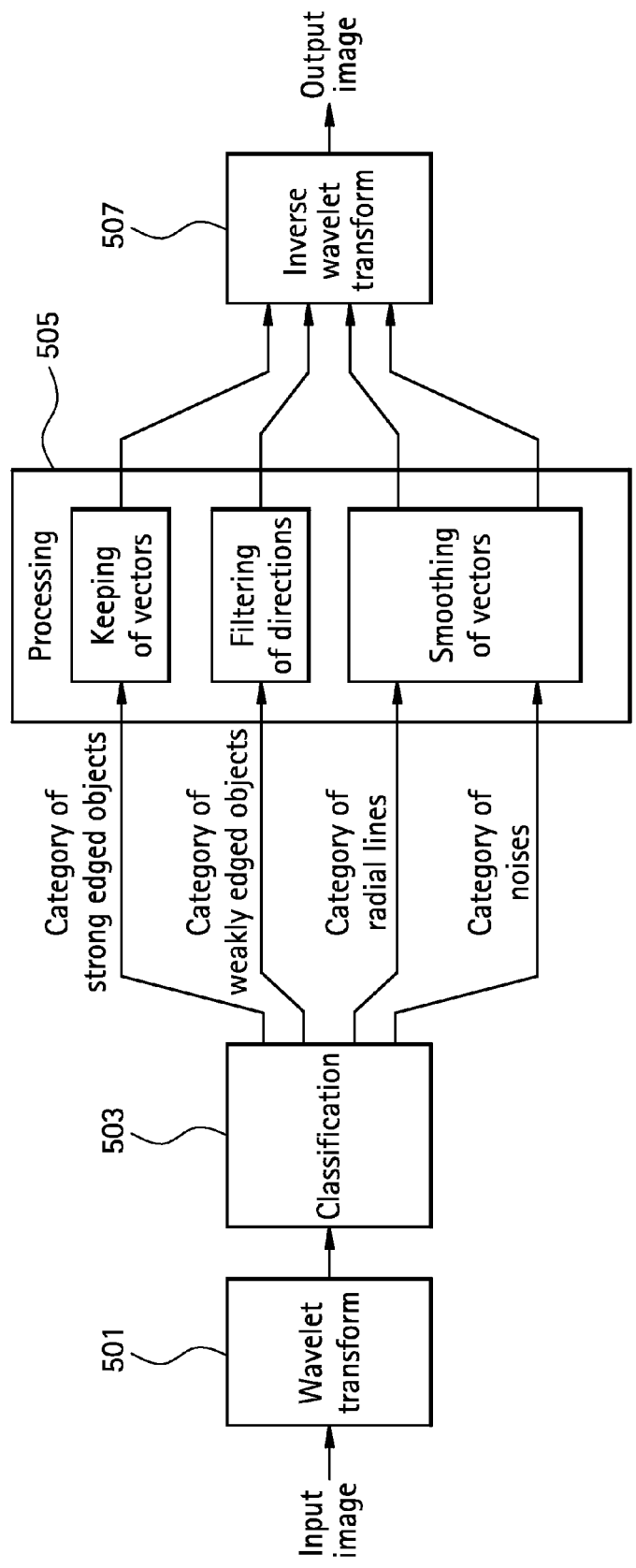
FIG. 5 describes a flow of image processing that is an example of the best mode for implementing the present invention.

Reducing noises contained in a reconstructed image will be described below. FIG. 5 describes a flow of noise reduction. The described noise reduction is achieved by a computer incorporated in the operator console 300.

As illustrated in FIG. 5, an input image is wavelet-transformed in stage 501. The computer that wavelet-transforms the input image in stage 501 is an example of a transforming means included in the present invention.

Wavelet transform is achieved according to the formula below.

$$\begin{bmatrix} W_{2j}^1 f(x,y) \\ W_{2j}^2 f(x,y) \end{bmatrix} = 2^j \begin{bmatrix} \frac{a}{ax}(f*\theta_{2j})(x,y) \\ \frac{a}{ay}(f*\theta_{2j})(x,y) \end{bmatrix} = 2^j \vec{\nabla}(f*\theta_{2j})(x,y) \quad \text{[Formula 1]}$$

The above formula is described in the IEEE Trans. Pattern Analysis and Machine Intelligence ("Characterization of Signals from Multiscale Edges" by Stephane Mallat and Sifen Zong, July 1992, Vol. 14(7), pp. 710-732).

The above formula expresses wavelet transform that employs a two-dimensional gradient form. The result of the transform is a two-dimensional distribution of wavelet vectors expressing edges of objects contained in an input image.

The two-dimensional distribution of wavelet vectors is an expression of an input image in the wavelet domain. The magnitude of a wavelet vector (representing an amplitude) indicates the strength of edging, and the direction of the wavelet vector indicates the direction of the edging. Hereinafter, the wavelet vector may simply be called a vector.

In stage 503, vectors are classified. The computer for classifying vectors in stage 503 is an example of a classifying means included in the present invention.

Two kinds of thresholds are employed in classification of vectors. One of the thresholds is concerned with the magnitude of a vector, and the other is concerned with the regulation in the direction of a vector.

The threshold concerning the magnitude of a vector defined in a scale j is provided as follows:

$$T = K\sigma 2^{-(j-1)/2} \quad \text{[Formula 2]}$$

where K denotes a constant, σ denotes a standard deviation of modules for $1^{st}$ scale wavelet vectors in a area which is uniform image, and j denotes a scale.

Two different values are determined as the values of the constant K, whereby two different thresholds Tg and Ts are determined for the magnitude of a vector. The threshold Tg is an example of a first threshold employed in the present invention, while the threshold Ts is an example of a second threshold employed in the present invention. The threshold Ts is smaller than the threshold Tg.

A threshold Tr is determined for the regulation in the direction of a vector. Assuming that a ratio of one vector to another vector is adopted as the measure of the regulation in the direction of a vector, the threshold Tr is determined for the ratio. The threshold Tr is an example of a third threshold employed in the present invention.

The ratio of vectors is the ratio of a mean vector, which is a mean of a center vector, which is located in the center of a window defined with a matrix of 3 by 3, and two ambient vectors whose differences from the center vector are the smallest to a mean vector that is a mean of all vectors in the window. By adopting the ratio of vectors, the regulation in the direction of a vector can be expressed simply.

The rules for classification based on the thresholds Tg, Ts, and Tr will be described below.

(1) Vectors whose magnitudes are larger than the threshold Tg are classified into a category of strongly edged objects.

(2) Vectors whose magnitudes are equal to or smaller than the threshold Tg and larger than the threshold Ts and whose regulations in directions thereof are larger than the threshold Tr are classified into a category of weakly edged objects.

(3) Vectors whose magnitudes are equal to or smaller than the threshold Tg and whose regulations in directions thereof are equal to or smaller than the threshold Tr are classified into a category of radial lines.

(4) Vectors whose magnitudes are equal to or smaller than the threshold Ts are classified into a category of noises.

Figures 6, 7:
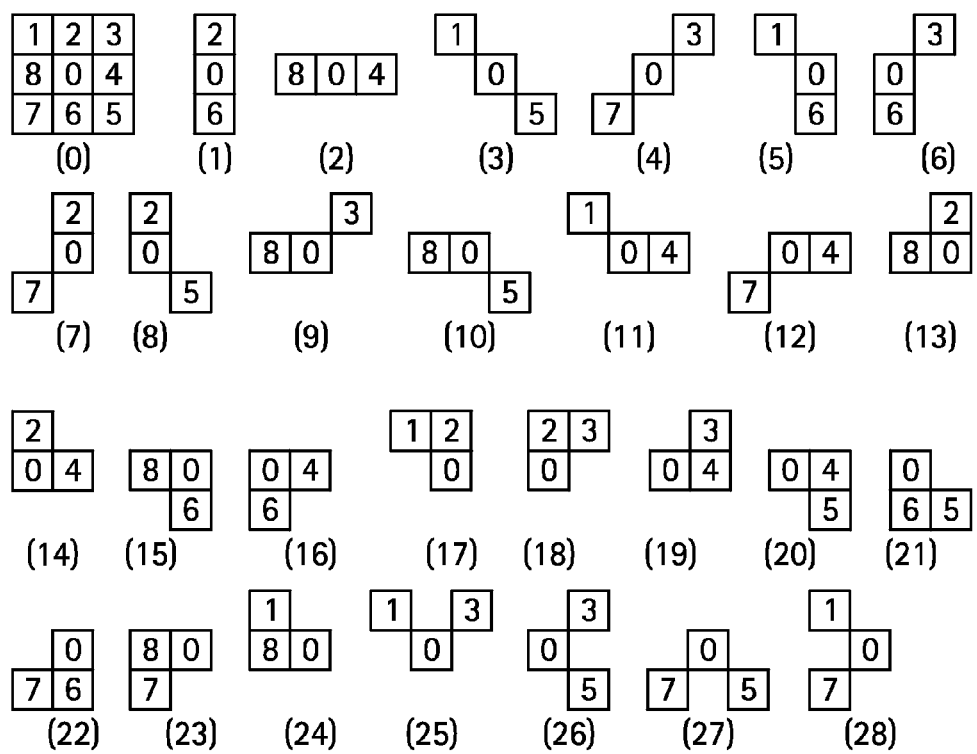
FIG. 6 shows the classification of wavelet vectors.
FIG. 7 shows directions to be filtered.

Through the classification performed based on the foregoing rules, vectors are classified into four categories of strongly edged objects, weakly edged objects, radial lines, and noises, as shown in FIG. 6. Incidentally, the radial line is an artifact.

The thus classified vectors are processed in different manners associated with the categories in stage 505. The computer for processing the vectors in stage 505 is an example of a processing means included in the present invention.

In stage 505, vectors classified into the category of strongly edged objects are kept, that is, left intact. In other words, the vectors classified into the category of strongly edged objects have the magnitudes and directions thereof left intact.

Vectors classified into the category of weakly edged objects have the directions thereof filtered. The filtering of directions is achieved by sampling a combination of a center vector, which is located in the center of a window defined with a matrix of 3 by 3, and two ambient vectors the sum of whose differences from the center vector is the smallest, and replacing the center vector with a mean vector that is a mean of the two ambient vectors and the center vector.

In a window defined with a matrix of 3 by 3 like the one shown in FIG. 7(0), assuming that the center position of the window is a position 0, a center vector exists at the center position 0, and ambient vectors exist at eight ambient positions 1 to 8. As shown in FIG. 7(1) to FIG. 7(28), twenty-eight combinations of the center vector and two ambient vectors are conceivable.

Among the combinations, a combination of the center vector and two ambient vectors the sum of whose differences from the center vector is the smallest is sampled, and the center vector is replaced with a mean vector that is a mean of the two ambient vectors and the center vector.

Owing to the foregoing filtering of directions, weakly edged objects become sharp. A mean vector with which a center vector is replaced may be multiplied by a variable coefficient. When the coefficient is made larger than 1, the clearness in the edges of the objects can be intensified. When the coefficient is smaller than 1, the clearness in the edges of the objects can be lessened.

Vectors classified into the categories of radial lines and noises are smoothed. The smoothing of vectors is achieved by replacing a center vector, which is located in the center of a window defined with a matrix of 3 by 3, with a mean vector that is a mean of all vectors in the window.

Figure 8A:
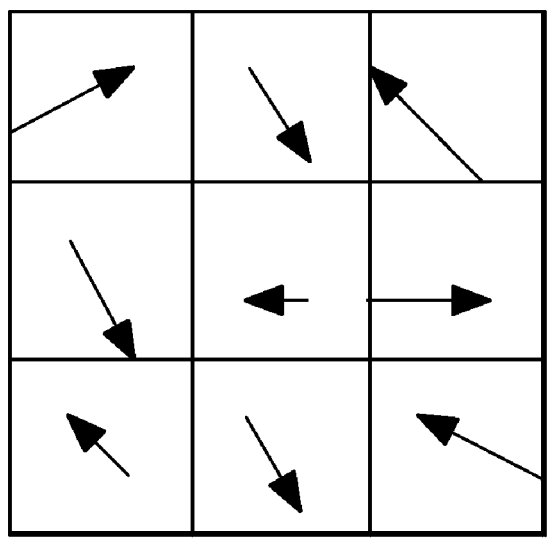
FIGS. 8a and 8b show the concept of smoothing of vectors.
Figure 8B:
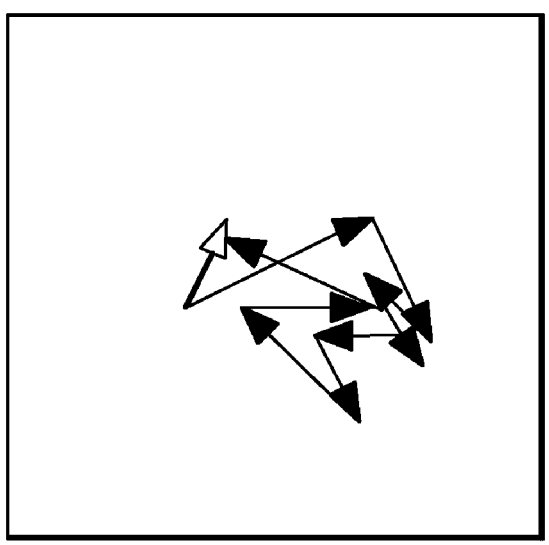

FIG. 8 is a conceptual diagram of the smoothing of vectors. Assuming that vectors within a window defined with a matrix of 3 by 3 are defined as shown in FIG. 8(*a*), a mean vector of all the vectors in the window is expressed as a blank vector shown in FIG. 8(*b*). A center vector is replaced with the mean vector. The smoothing of vectors lessens radial lines and noises.

The four kinds of vectors having been processed as mentioned above are inverse-wavelet-transformed in stage 507. The computer for performing inverse wavelet transform in stage 507 is an example of an image production means included in the present invention.

The inverse wavelet transform is inverse wavelet transform using a two-dimensional gradient form. The inverse wavelet transform restores a real-domain image.

FIG. 9 conceptually shows the foregoing signal processing. In FIG. 9, an image signal is regarded as a one-dimensional signal. FIG. 9(a) indicates the strength of an input image signal. The strengths of the components of the signal representing objects are relatively large, but the strengths of the components thereof representing noises and radial lines are relatively small.

Wavelet transform provides a wavelet-domain image like the one shown in FIG. 9(b). Herein, an image portion defined in one scale j is shown. The components of a signal representing the image portion whose strengths are larger than a threshold Tg represent strongly edged objects. The component of the signal whose strength is equal to or smaller than the threshold Tg and larger than a threshold Ts and whose regulation is larger than a threshold Tr represents a weakly edged object. The component of the signal whose strength is equal to or smaller than the threshold Tg and whose regulation is equal to or smaller than the threshold Tr represents a radial line. The components of the signal whose strengths are equal to or smaller than the threshold Ts represent noises.

The signal is recomposed into a signal shown in FIG. 9(c) through classification and processing. The strengths of the components of the signal representing the strongly edged object remain unchanged. The strength of the component thereof representing the weakly edged object is improved so that the weakly edged object will become sharp. The components thereof representing the radial line and noises are lessened.

The signal is inverse-wavelet-transformed to finally represent a real-domain output image in the manner as shown in FIG. 9(d). The strengths of the components of the resultant signal representing the output image which represent objects remain unchanged compared with those of the corresponding components of a signal representing an input image, but the strengths of the components thereof which represent a radial line and noises are lower than those of the corresponding components of the signal representing the input image. Namely, the radial line and noises in the image can be reduced without occurrence of a shift in a CT number, deformation of edges, or an abrupt change. Moreover, since a component of a wavelet-domain signal expressing a weakly edged object has the directions thereof filtered, the fine structure of the object becomes clear.

Figure 10:
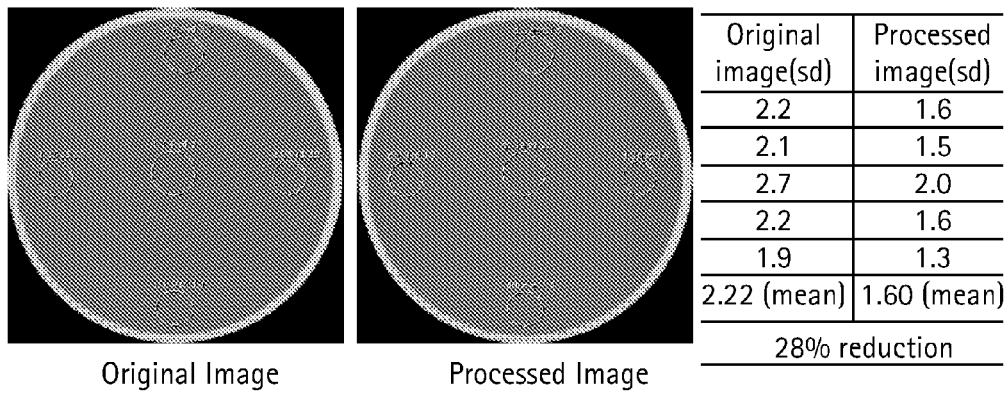
FIG. 10 shows comparison between an original image and a processed image using partly half-tone photographs.

FIG. 10 to FIG. 13 show examples of improvements in image quality derived from the foregoing image processing. FIG. 10 shows an original image produced by projecting a uniform phantom, a processed image, and a comparison of standard deviations sd of pixels at five positions in the original image with those of corresponding pixels in the processed image. A mean of the standard deviations in the processed image is 28% smaller. Thus, noises are reduced markedly.

Figure 11:
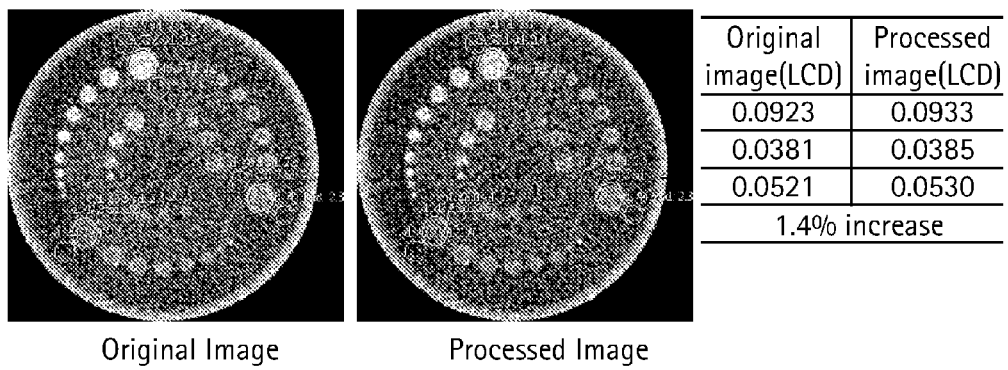
FIG. 11 shows comparison between an original image and a processed image using partly half-tone photographs.

FIG. 11 shows an original image produced by projecting a low-contrast density (LCD) phantom, a processed image, and a comparison of contrast resolutions (LCDs) detected at three points in the original image with those detected in the processed image. The LCDs in the processed images are 1.4% larger than those in the original image. Thus, the contrast resolution is markedly improved due to noise reduction.

Figure 12:
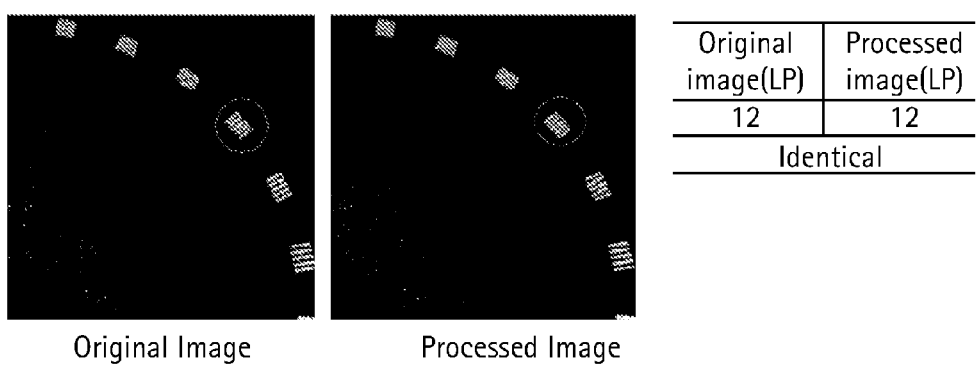
FIG. 12 shows comparison between an original image and a processed image using partly half-tone photographs.

FIG. 12 shows an original image produced by projecting a spatial-resolution phantom, a processed image, and a comparison of a spatial resolution (or a degree of line partition (LP)) in the original image with that in the processed image. The spatial resolution (LP) in the processed image is identical to that in the original image. This means that the spatial resolution is not degraded.

FIG. 13 shows an original image (a) produced by projecting a Modulation Transfer Function (MTF) phantom, a processed image (b), and a comparison (c) of Modulation Transfer Functions describing the relationships between values detected in the original image and values detected in the processed image. The Modulation Transfer Functions are retained at specified values. This means that the Modulation Transfer Functions are not fluctuated.

The invention claimed is:

1. An image processing method comprising the steps of:
    wavelet-transforming an input image using a gradient form;
    classifying resultant wavelet vectors into categories of strongly edged objects, weakly edged objects, radial lines, and noises;
    leaving the wavelet vectors, which are classified into the category of strongly edged objects, intact;
    filtering the directions of the wavelet vectors classified into the category of weakly edged objects;
    smoothing the wavelet vectors classified into the categories of radial lines and noises; and
    inverse-wavelet-transforming the resultant wavelet vectors so as to produce an output image.

2. The image processing method according to claim 1, wherein:
    the classification employs a first threshold concerning the magnitude of a vector, a second threshold smaller than the first threshold, and a third threshold concerning the regulation in the direction of a vector;
    wavelet vectors whose magnitudes are larger than the first threshold are classified into the category of strongly edged objects;
    wavelet vectors whose magnitudes are equal to or smaller than the first threshold and larger than the second threshold and whose regulations in directions thereof are larger than the third threshold are classified into the category of weakly edged objects;
    wavelet vectors whose magnitudes are equal to or smaller than the first threshold and whose regulations in directions thereof are equal to or smaller than the third threshold are classified into the category of radial lines; and
    wavelet vectors whose magnitudes are equal to or smaller than the second threshold are classified into the category of noises.

3. The image processing method according to claim 2, wherein the regulation in the direction of a vector is expressed as a ratio of a mean vector, which is a mean of a center vector located in the center of a window defined with a matrix of 3 by 3 and two ambient vectors whose differences from the center vector are the smallest, to a mean vector that is a mean of all vectors in the window.

4. The image processing method according to claim 1, wherein the filtering of directions is achieved by sampling a combination of a center vector located in the center of a window defined with a matrix of 3 by 3 and two ambient vectors the sum of whose differences from the center vector is the smallest, and replacing the center vector with a mean vector that is a mean of the two ambient vectors and the center vector.

5. The image processing method according to claim 1, wherein the smoothing of vectors is achieved by replacing a center vector, which is located in the center of a window defined with a matrix of 3 by 3, with a mean vector that is a mean of all vectors in the window.

6. An X-ray CT system comprising a data acquisition means for acquiring data by scanning a subject with X-rays, an image reconstruction means for reconstructing an image on the basis of the acquired data, and an image processing means for processing the reconstructed image, wherein:

the image processing means comprises:

a transforming means for wavelet-transforming an input image using a gradient form;

a classifying means for classifying resultant wavelet vectors into categories of strongly edged objects, weakly edged objects, radial lines, and noises;

leaving the wavelet vectors, which are classified into the category of strongly edged objects, intact;

filtering the directions of the wavelet vectors classified into the category of weakly edged objects;

smoothing the wavelet vectors classified into the categories of radial lines and noises; and inverse-wavelet-transforming the resultant wavelet vectors so as to produce an output image.

7. The X-ray CT system according to claim 6, wherein:

the classification employs a first threshold concerning the magnitude of a vector, a second threshold smaller than the first threshold, and a third threshold concerning the regulation in the direction of a vector;

wavelet vectors whose magnitudes are larger than the first threshold are classified into the category of strongly edged objects;

wavelet vectors whose magnitudes are equal to or smaller than the first threshold and larger than the second threshold and whose regulations in directions thereof are larger than the third threshold are classified into the category of weakly edged objects;

wavelet vectors whose magnitudes are equal to or smaller than the first threshold and whose regulations in directions thereof are equal to or smaller than the third threshold are classified into the category of radial lines; and wavelet vectors whose magnitudes are equal to or smaller than the second threshold are classified into the category of noises.

8. The X-ray CT system according to claim 7, wherein the regulation in the direction of a vector is expressed as a ratio of a mean vector, which is a mean of a center vector located in the center of a window defined with a matrix of 3 by 3 and two ambient vectors whose differences from the center vector are the smallest, to a mean vector that is a mean of all vectors in the window.

9. The X-ray CT system according to claims 6, wherein the filtering of directions is achieved by sampling a combination of a center vector, which is located in the center of a window defined with a matrix of 3 by 3, and two ambient vectors the sum of whose differences from the center vector is the smallest, and replacing the center vector with a mean vector that is a mean of the two ambient vectors and the center vector.

10. The X-ray CT system according to any of claims 6, wherein the smoothing of vectors is achieved by replacing a center vector, which is located in the center of a window defined with a matrix of 3 by 3, with a mean vector that is a mean of all vectors in the window.

* * * * *